United States Patent [19]
Wright

[11] 4,013,085
[45] Mar. 22, 1977

[54] DENTAL CLEANING MEANS AND METHOD OF MANUFACTURE THEREFOR

[76] Inventor: Charles E. Wright, 3167 Bayview Ave., Willowdale, Ontario, Canada, M2K 1G2

[22] Filed: Feb. 17, 1976

[21] Appl. No.: 658,197

Related U.S. Application Data

[63] Continuation of Ser. No. 489,134, July 17, 1974, abandoned.

[52] U.S. Cl. .................................................. 132/89
[51] Int. Cl.² ........................................ A61C 15/00
[58] Field of Search ............. 132/89, 90, 91, 92 A, 132/93

[56] References Cited

UNITED STATES PATENTS

| 788,947 | 5/1905 | Roth | 132/91 |
|---|---|---|---|
| 1,456,279 | 5/1923 | Patterson | 132/92 A |
| 2,187,899 | 1/1940 | Henne | 132/92 |
| 3,247,857 | 4/1966 | Kanbar | 132/93 |
| 3,802,445 | 4/1974 | Wesley | 132/89 |

Primary Examiner—G.E. McNeill
Attorney, Agent, or Firm—Irving M. Weiner; Pamela S. Austin

[57] ABSTRACT

This invention provides a dental 'floss' of an oriented monofilamentous polymer together with a method of manufacturing the 'floss' and a tool for its use.

3 Claims, 5 Drawing Figures

DENTAL CLEANING MEANS AND METHOD OF MANUFACTURE THEREFOR

This application is a continuation of application Ser. No. 489,134 filed July 17, 1974 now abandoned.

This invention relates to dental cleansing tools, and, more particularly, to dental floss.

BACKGROUND OF THE INVENTION

Previously, dental floss has comprised a multi-filament twisted strand of various materials which has sufficient flexibility to permit it to be placed between, and drawn through the spaces between adjacent teeth.

Normally, this dental floss is dispensed from a spool and in use has, unless the user is particularly dexterous, to be held between two hands.

However, the shortcomings of the prior dental floss have not been limited to its use. Its method of manufacture has been expensive. The necessity to produce plural individual filaments and then strand and wind on spools has been complicated and expensive.

The actual usage has also been wasteful. The user normally pulls a random length from the spool which may be too short but which is inevitably too long.

SUMMARY OF THE INVENTION

It is, therefore, the principal object of the present invention to provide an improved method of manufacturing dental floss, and an improved tool for its use which will permit more economic manufacturing, more facile dispensing and use.

In accordance with these objects there is provided in accordance with the present invention dental cleaning means which comprises an intermediate elongate flexible member of reduced width and thickness and a pair of wider terminal portions one adjacent each end.

There is further provided in accordance with the present invention dental cleaning means which comprises a plurality of substantially parallel spaced apart elongate members of reduced width and thickness and a second plurality of wider, thicker terminal members one adjacent each end of said elongate members, each said wider member being separably connected to adjacent wider members.

Further in accordance with the present invention there is provided a method of manufacturing dental cleaning means comprising the steps of:

a. forming from a substantially continuous web of molecularly unoriented polymeric material;

b. removing intermediate regular spaced apart sections from said web to provide a plurality of spaced apart members;

c. stretching said web substantially transversely whereby said members are uniaxially oriented along their respective longitudinal axes.

There objects and features will be more apparent from the following drawings and description in which specific embodiments are given by way of example and in which.

Figures 1, 2:
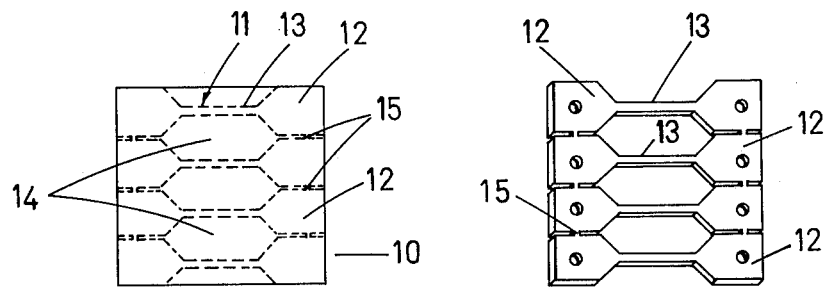
FIG. 1 is a plan view of a web of material employed in producing the dental floss in accordance with the present invention.
FIG. 2 is an isometric view of an intermediate formation of dental floss in accordance with the present invention.

In FIG. 1 of the drawings there is shown a web 10 of thin flexible thermoplastic material in which the cuts to be made in the web are shown in dotted outline 11. The lines define future terminal portions 12 and elongate intermediate sections 13. The areas indicated at 14 are future open areas.

The thermoplastic material of the web may be polyamide, polyurethane, polyethylene or any of the higher polymers such as polypropylene.

It has been found that mechanical properties of such plastics can be improved considerably by transverse and/or longitudinal stretching; this property together with the reduced cost which ensues from the provision of a relatively longer member from the same amount of material as previously leads to considerable economy without loss of strength.

It is essential that dental floss have the capacity to pass between the adjacent teeth. To this end such conventional floss may require to be compressible. However, the floss which is to be described because of its two dimensions being of different gauges or dimensions may be engaged and disengaged with adjacent teeth by twisting. The provision of an edge permits easier cleaning and the fact that the "edge" is not sharp and the material being polymeric permits cleaning without cutting the gums.

To manufacture dental floss in accordance with the present invention, web 10 is initially die cut along the dotted lines shown in FIG. 1 so that it has the form shown in FIG. 2 with terminal portions 12 and the elongate intermediate portions 13. Terminal portions 12 are each connected to their neighbouring terminal portions 12 on either side thereof. This interconnection permits separation while maintaining continuity through manufacturing and dispensing. Web 10 may have an initial thickness of 10 mils. Subsequently, the intermediate elongate portions 13 are stretched transversely. This may be accomplished by passing the die cut web 10 over a conveyor with a gradually widening track. Clamps or suitable gripping devices are provided along the conveyor which engage the terminal portions 12, and move in concert therewith so that, as the conveyor moves, the intermediate elongate portions 13 are stretched laterally and linearly oriented while the terminal portions 12 are not stretched. If necessary, heat may be applied to the intermediate portions 13 of the web to facilitate stretching in any suitable manner.

The lateral stretching gives the intermediate portions 13 an uniaxial molecular orientation and increased tensile strength in the direction of stretching.

Figure 3:
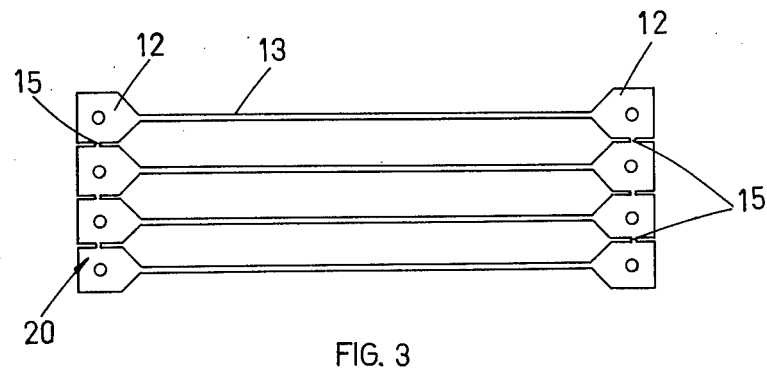
FIG. 3 is a plan view of dental floss in accordance with the present invention.
Figure 4:
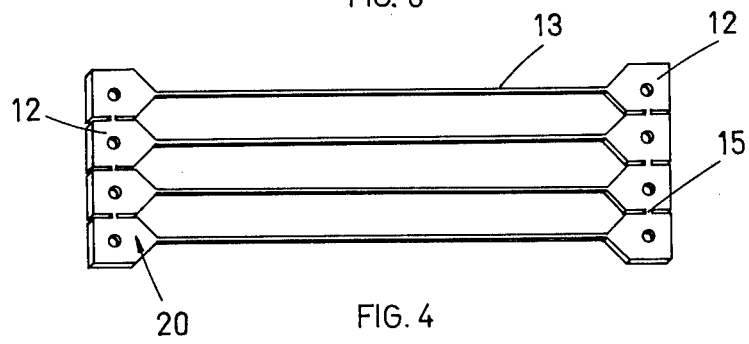
FIG. 4 is an isometric view of the floss of FIG. 3.
Figure 5:
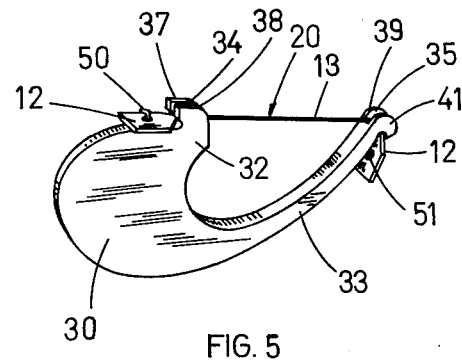
FIG. 5 is an isometric view of a new dental tool for use in association with dental floss in accordance with the present invention.

The final product of the stretching operation is as shown in FIGS. 3 and 4. The length of the intermediate portions 13 has been increased six times and their thickness has decreased to one third of its original thickness. This structure can then be rolled and packaged in units of ten individual "pieces" of "floss" 20 interconnected by links such as 15.

When the user requires to clean his teeth, he selects a terminal piece and merely separates it by breaking off at the links 15 to provide floss 20.

The floss 20 may be used by mounting it on the tool 30. This tool comprises a substantially flat handle 31 with arms 32 and 33 extending therefrom in the same plane as shown. One of these arms is preferably longer than the other for ease of use. At the end of each arm, a notch such as 34 and 35 on arms 32 and 33 with outward projections 37 and 38 and 39 and 41 are provided, and the floss 20 engages therewith so that the terminal portions 12 engage with the notches on the remote side from the gap defined by the arms 32 and 33. If desired, other forms such as hooks 50 and 51 or latches for engaging the hooks on the wider portions may be provided as shown.

After the "floss" has been mounted on the tool 30, it is used by inserting the tool in the mouth so that the elongate portion 13 is aligned with the tooth gap to be cleaned. A gentle sawing motion will then effect cleaning. The edges of the intermediate portion 13 will engage the tooth or teeth and effectively clean without damage.

From the foregoing it will be apparent that, in the present invention, the dental floss provided is economical to manufacture, and convenient to use. It will, of course, also be apparent that other alternative forms of "floss" may be provided without departing from the scope of the claims annexed hereto.

What I claim is:

1. Dental cleaning means comprising an elongated strip of polymeric material, said strip having terminal portions removably securable to a holder and connected by a flat unitary flexible elongated intermediate member integral therewith, said intermediate member being of reduced width and thickness compared to said terminal portions for insertion between the teeth for tooth cleaning purposes, said flexible elongated intermediate member being of substantially linearly molecularly oriented polymeric material and said terminal portions being of substantially molecularly unoriented polymeric material.

2. Dental cleaning means according to claim 1 including a plurality of said elongated strips of polymeric material in side by side relationship, each terminal portion of each strip being separably connected by an integral breakable link to a corresponding terminal portion of an adjacent strip.

3. A method of manufacturing dental cleaning means comprising:
   a. removing intermediate regularly spaced portions from a web of molecularly unoriented polymeric material to form a plurality of transversely extending elongated strips in side by side relationship, each strip having terminal portions connected by an intermediate member of reduced width compared to said terminal portions and integral therewith, each terminal portion of each strip being separably connected by an integral breakable link to a corresponding terminal portion of an adjacent strip, and
   b. stretching said web transversely to substantially linearly molecularly orientate the intermediate members with reduction in thickness and width thereof while leaving said terminal portions substantially molecularly unoriented.

* * * * *